United States Patent
Claussen et al.

(10) Patent No.: US 12,194,113 B2
(45) Date of Patent: Jan. 14, 2025

(54) MICROCAPSULE WITH A POROUS OR HOLLOW CORE AND PH-SENSITIVE SHELL AND USE THEREOF

(71) Applicant: Solventum Intellectual Properties Company, Maplewood, MN (US)

(72) Inventors: Kai U. Claussen, Munich (DE); Silke D. Mechernich, Düsseldorf (DE); Mareike Richter, Düsseldorf (DE); Reinhold Hecht, Kaufering (DE); Manfred Ludsteck, Geretsried (DE); Simone Jurjevic, Neuss (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 199 days.

(21) Appl. No.: 16/967,937

(22) PCT Filed: Feb. 1, 2019

(86) PCT No.: PCT/IB2019/050820
§ 371 (c)(1),
(2) Date: Aug. 6, 2020

(87) PCT Pub. No.: WO2019/155334
PCT Pub. Date: Aug. 15, 2019

(65) Prior Publication Data
US 2020/0368117 A1    Nov. 26, 2020

(30) Foreign Application Priority Data
Feb. 6, 2018 (EP) .................................. 18155210

(51) Int. Cl.
*A61K 6/889* (2020.01)
*A61C 5/00* (2017.01)
(Continued)

(52) U.S. Cl.
CPC ............... *A61K 6/889* (2020.01); *A61C 5/00* (2013.01); *A61C 7/00* (2013.01); *A61K 6/17* (2020.01); *C08F 222/10* (2013.01)

(58) Field of Classification Search
None
See application file for complete search history.

(56) References Cited

U.S. PATENT DOCUMENTS

| 4,642,126 A | 2/1987 | Zador |
| 4,652,274 A | 3/1987 | Boettcher |

(Continued)

FOREIGN PATENT DOCUMENTS

| EP | 0038585 | 7/1984 |
| WO | WO 1998-07324 | 2/1998 |

(Continued)

OTHER PUBLICATIONS

J.-W. Kim, Y.-G. Joe, and K.-D. Suh. "Poly(methyl methacrylate) hollow particles by water-in-oil-in-water emulsion polymerization." Colloid and Polymer Science, vol. 277, 1999, pp. 252-256. (Year: 1999).*

(Continued)

*Primary Examiner* — Isaac Shomer

(57) ABSTRACT

The invention relates to a microcapsule comprising a hollow or porous core, the hollow or porous core being composed of a polymeric material and containing a component of a redox-initiator system, a shell, the shell being composed of a pH-sensitive material. The microcapsule can be used for formulating dental materials.

16 Claims, 2 Drawing Sheets

(51) Int. Cl.
*A61C 7/00* (2006.01)
*A61K 6/17* (2020.01)
*C08F 222/10* (2006.01)

(56) References Cited

U.S. PATENT DOCUMENTS

| | | | |
|---|---|---|---|
| 4,737,593 A | | 4/1988 | Ellrich |
| 4,795,823 A | | 1/1989 | Schmitt |
| 5,053,436 A | * | 10/1991 | Delgado ............... C09J 133/06 |
| | | | 521/64 |
| 5,154,762 A | | 10/1992 | Mitra |
| 5,918,772 A | | 7/1999 | Keller |
| 5,944,419 A | | 8/1999 | Streiff |
| 6,022,501 A | | 2/2000 | Dexter |
| 6,149,953 A | | 11/2000 | Redding, Jr. |
| 6,391,288 B1 | | 5/2002 | Miyazawa |
| 6,403,119 B2 | | 6/2002 | Oppenheim |
| 6,444,725 B1 | | 9/2002 | Trom |
| 7,214,726 B2 | | 5/2007 | Qian |
| 7,838,037 B2 | | 11/2010 | Kvitnitsky |
| 8,182,831 B2 | | 5/2012 | Lin |
| 9,422,411 B2 | | 8/2016 | Sahouani |
| 2003/0148013 A1 | | 8/2003 | Jobe |
| 2004/0224019 A1 | | 11/2004 | Shefer |
| 2006/0187752 A1 | | 8/2006 | Keller |
| 2007/0088097 A1 | * | 4/2007 | Qian .................. A61K 6/887 |
| | | | 523/115 |
| 2007/0090079 A1 | | 4/2007 | Keller |
| 2010/0021549 A1 | | 1/2010 | Meyrueix |
| 2010/0330150 A1 | * | 12/2010 | Venkatesh .......... A61K 45/06 |
| | | | 514/315 |
| 2011/0171275 A1 | * | 7/2011 | Jiang .................. A61P 25/18 |
| | | | 514/342 |
| 2013/0034602 A1 | | 2/2013 | Qian |
| 2016/0088836 A1 | * | 3/2016 | Sahouani ............ A01N 47/44 |
| | | | 514/635 |
| 2016/0332131 A1 | * | 11/2016 | Lee .................. C11D 3/505 |
| 2016/0339141 A1 | * | 11/2016 | Gann .................. A61K 8/22 |

FOREIGN PATENT DOCUMENTS

| | | |
|---|---|---|
| WO | WO 2005-016783 | 2/2005 |
| WO | WO 2006-127686 | 11/2006 |
| WO | WO 2007-013794 | 2/2007 |
| WO | WO 2007-104037 | 9/2007 |
| WO | WO 2008-035229 | 3/2008 |
| WO | WO 2008-091228 | 7/2008 |
| WO | WO 2009-061884 | 5/2009 |
| WO | WO 2010-123800 | 10/2010 |
| WO | WO 2014-064255 | 5/2014 |
| WO | WO 2014-186328 | 11/2014 |
| WO | WO 2014-186336 | 11/2014 |
| WO | WO 2015-073246 | 5/2015 |
| WO | WO 2016-007453 | 1/2016 |
| WO | WO 2016-053830 | 4/2016 |
| WO | WO 2017-178297 | 10/2017 |
| WO | WO-2017178297 A1 * | 10/2017 ............ B01J 13/043 |

OTHER PUBLICATIONS

Pharma Excipients. https://www.pharmaexcipients.com/product/kollicoat-smartseal-30-d/ accessed Jan. 6, 2023, pp. 1-3. (Year: 2023).*
V. Kumar, T. Yang, Y. Yang. "Interpolymer complexation. I. Preparation and characterization of a polyvinyl acetate phthalate-polyvinylpyrrolidone (PVAP-PVP) complex." International Journal of Pharmaceutics, vol. 188, 1999, pp. 221-232. (Year: 1999).*
Julia A. Barman Balfour and Greg L. Plosker. "Rosiglitazone." Drugs, vol. 57(6), Jun. 1999, pp. 921-930. (Year: 1999).*
S. Victoria Otton et al. "CYP2D6 phenotype determines the metabolic conversion of hydrocodone to hydromorphone." Clinical Pharmacology & Therapeutics, vol. 54, No. 5, Nov. 1993, pp. 463-472. (Year: 1993).*
Ch. Niranjan Patra, Richa Priya, Suryakanta Swain, Goutam Kumar Jena, Kahnu Charan Panigrahi, Debashish Ghose. "Pharmaceutical significance of Eudragit: A review." Future Journal of Pharmaceutical Sciences, vol. 3, 2017, pp. 33-45. (Year: 2017).*
Seema Thakral, Naveen K Thakral & Dipak K Majumdar. "Eudragit®: a technology evaluation." Expert Opinion on Drug Delivery, vol. 10:1, 2013, pp. 131-149 and an additional title page. (Year: 2013).*
Esser-Kahn, "Triggered Release from Polymer Capsules", Macromolecules, Jul. 2011, vol. 44, No. 14, pp. 5539-5553.
International Search Report for PCT International Application No. PCT/IB2019/050820, mailed on Apr. 24, 2019, 5 pages.

* cited by examiner

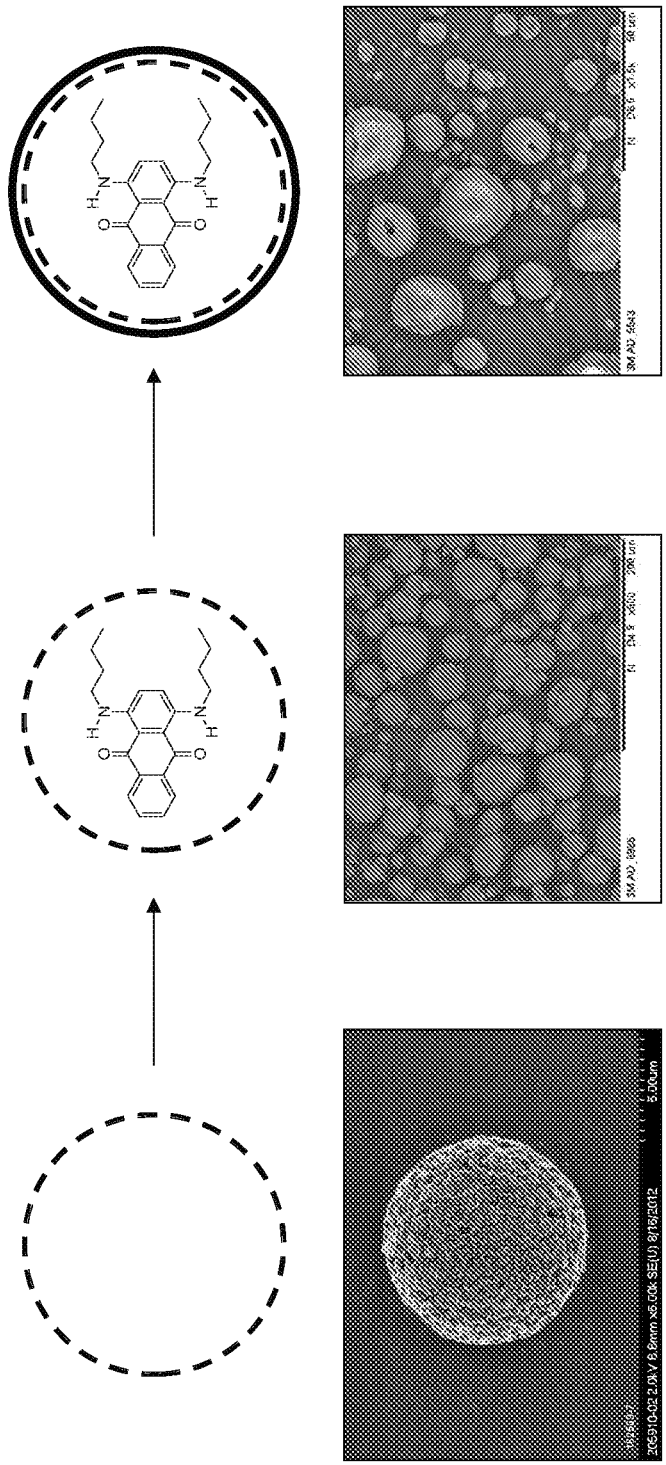

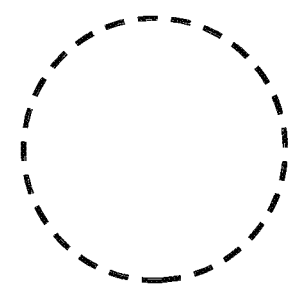
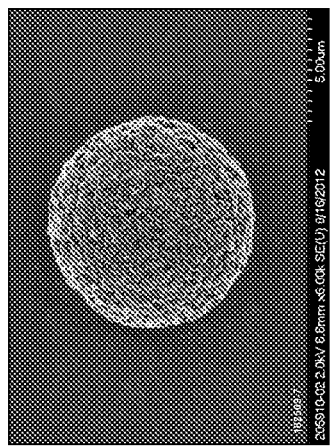
FIG. 2A
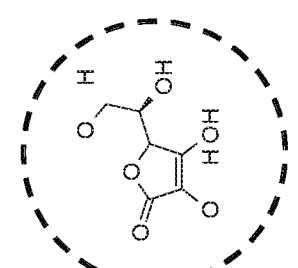
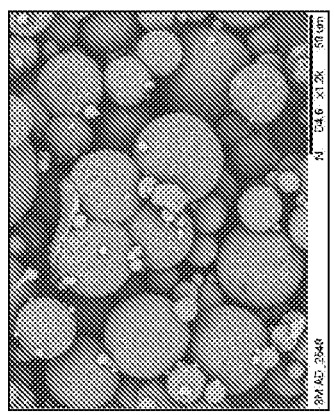
FIG. 2B
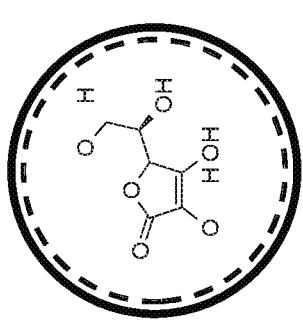
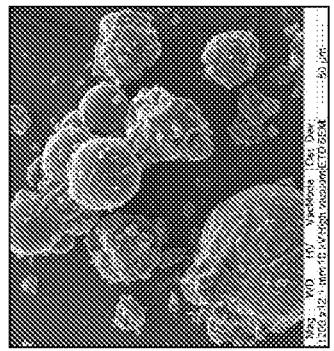
FIG. 2C

MICROCAPSULE WITH A POROUS OR HOLLOW CORE AND PH-SENSITIVE SHELL AND USE THEREOF

CROSS REFERENCE TO RELATED APPLICATIONS

This application is a national stage filing under 35 U.S.C. 371 of PCT/IB2019/050820, filed 1 Feb. 2019, which claims the benefit of European Patent Application No. 18155210.0, filed 6 Feb.2018, the disclosures of which are incorporated by reference in their entirety herein.

FIELD OF THE INVENTION

The invention relates to a pH-sensitive microcapsule, a paste/paste system containing such a microcapsule and its use for producing a curable composition comprising a redox-initiator system.

BACKGROUND

The use of microcapsules for storing components of redox initiator systems is generally known.

U.S. Pat. No. 5,154,762 (Mitra et al.) describes in example 11 the microencapsulation of ascorbic acid in cellulose acetate butyrate. It is stated that although the use of water-insoluble encapsulants may initially seem inappropriate in water-based cements, it was found that vigorous mechanical mixing generally is sufficient to break apart the capsule walls and permit adequate release of the encapsulated reducing agent or oxidizing agent and subsequent cure of the cement. This technology is particularly useful for preparing powder compositions.

However, compared to paste/paste systems powder compositions are easier to prepare and stabilize due to the physical separation of the powder components to be mixed.

In contrast thereto, pasty compositions are typically manufactured by kneading processes where high shear forces are applied onto the microcapsules.

The microcapsules described in the prior art, in particular those suggested for storing components of a redox-initiator system, are typically not sufficiently stable to survive such high shear forces.

On the other hand, when mixing paste/paste compositions the applied mixing forces are often not sufficiently strong enough for breaking the microcapsules to enable the release of the active reagents.

Therefore, the technology used for producing powder compositions can typically not be used for paste/paste compositions. Other references which describe the use and production of microcapsules are:

U.S. Pat. No. 9,422,411 B2 (Sahouani et al.) relates to porous polymeric particles that can be hydrophilic or hydrophobic. The porous polymeric particles can be used for the storage and delivery of various active agents or for moisture management. Reaction mixtures for forming the porous polymeric particles, methods of making the porous polymeric particles, and articles containing the porous polymeric particles are also provided.

US 2016/088836 A1 (Sahouani et al) describes polymeric composite particles that can be used for the storage and delivery of various biologically active agent. The polymeric composite particles contain a porous polymeric core and a coating layer around the porous polymeric core. The porous polymeric composite particles typically further include a biologically active agent positioned within the porous polymeric core but not covalently bonded to the porous polymeric core. The biologically active agent can be released from the polymeric composite particle by diffusing out of the porous polymeric core through the coating layer.

WO 2016/053830 A1 (3M IPC) describes articles that include a fibrous substrate and porous polymeric particles. At least 50% of the porous polymeric particles are bound to the fibrous substrate. Methods of making the articles are provided that include providing porous polymeric particles, providing a fibrous substrate, and binding the porous polymeric particles to the fibrous substrate. The articles can be used for fluid management.

U.S. Pat. No. 6,391,288 B1 (Miyazawa et al) describes the preparation of microcapsules comprising an inner oil phase, a water phase and an outer oil phase. Ascorbic acid (in the water phase) is encapsulated. The microcapsules have a fracture strength of 10-500 $g/cm^2$ or 500-2,000 $g/cm^2$ or 2,000-5,000 $g/cm^2$. O/w emulsions are used to produce the microcapsules. The release of the active ingredient such as ascorbic acid can be triggered by an appropriate rupture strength.

SUMMARY OF INVENTION

Thus, there is a desire for microcapsules which can be used for producing storage-stable, redox-curable, pasty compositions.

Further, it should be possible to ensure a proper release of the components stored in the microcapsules on demand.

This object is addressed by the microcapsules and related processes described in the claims and the present text.

In one embodiment, the invention features a microcapsule as described in the claims and the present text.

In another embodiment, the invention relates to a kit of parts comprising a catalyst paste and a base paste comprising a pH-sensitive microcapsule as described in the claims and the present text.

A further embodiment of the invention is directed to a process for producing such a pH-sensitive microcapsule as described in the claims and the present text.

The invention is also related to a process of curing a curable composition containing microcapsules as described in the claims and the present text.

Moreover, the invention features the use of a microcapsule for producing a curable composition comprising a redox-initiator system as described in the claims and the present text.

The microcapsules essentially consist of a mechanically stable hollow or porous core which is filled with an active reagent and covered with a pH-sensitive shell that swells or dissolves in an acidic or basic environment.

The microcapsules are sufficiently stable to survive mixing processes including kneading processes which are typically applied for the preparation of pasty compositions.

BRIEF DESCRIPTION OF FIGURES

FIG. 1A-C shows SEM pictures of microcapsules described in the present text containing a dye and coated with an acid-sensitive material.

FIG. 2A-C shows SEM pictures of microcapsules described in the present text containing a reducing agent and coated with an acid-sensitive material.

Unless defined differently, for this description the following terms shall have the given meaning:

A "hollow core" refers to polymeric particles having a polymeric outer shell surrounding an inner region or cavity that is not polymeric.

A "porous core" refers to polymeric particles having a polymeric structure containing voids or pores.

As used herein, "(meth)acryl" is a shorthand term referring to "acryl" and/or "methacryl". For example, a "(meth) acryloxy" group is a shorthand term referring to either an acryloxy group (i. e., $CH_2=CH—C(O)—O—$) and/or a methacryloxy group (i.e., $CH_2=C(CH_3)—C(O)—O—$).

An "initiator" is a substance being able to initiate a chemical reaction, preferably via a free radical reaction. The initiator can be a single compound or can comprise more than one component, such as a combination of a sensitizing agent with a reducing agent. Depending on the reaction conditions chosen (e.g. pH-value >7 or pH-value <7) different initiators can be preferred.

A "redox initiator system" is defined as the combination of reducing agent(s) and oxidizing agent(s) being located on the application part of the application device. If present, transition metal component(s) are also regarded as components of the redox initiator system.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals, effective to polymerize ethylenically unsaturated compounds) involving one or more materials included in the composition.

A "dental composition" or a "composition for dental use" or a "composition to be used in the dental field" is any composition which can be used in the dental field. In this respect, the composition should be not detrimental to the patients' health and thus be free of hazardous and toxic components being able to migrate out of the composition. Examples of dental compositions include permanent and temporary crown and bridge materials, artificial crowns, anterior or posterior filling materials, adhesives, mill blanks, lab materials, luting agents and orthodontic devices. Dental compositions are typically hardenable compositions, which can be hardened at ambient conditions, including a temperature range of 15 to 50° C. or from 20 to 40° C. within a time frame of 30 min or 20 min or 10 min. Higher temperatures are not recommended as they might cause pain to the patient and may be detrimental to the patient's health. Dental compositions are typically provided to the practitioner in comparable small volumes, that is volumes in the range of 0.1 to 100 ml or 0.5 to 50 ml or 1 to 30 ml. Thus, the storage volume of useful packaging devices is within these ranges.

The term "compound" or "component" is a chemical substance which has a particular molecular identity or is made of a mixture of such substances, e.g., polymeric substances.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (methyl)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

"Polymer" or "polymeric material" are used interchangeably to refer to a homopolymer, copolymer, terpolymer etc.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A component comprising an "ascorbic acid moiety" is a component comprising the following structural element:

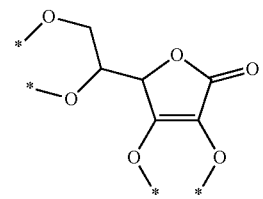 [SMILES: *OCC(O*)C1OC(=O)C(O*)=C1O*]

wherein the symbol "*" indicates a connection to another chemical moiety or atom.

"Ambient conditions" mean the conditions which the inventive composition is usually subjected to during storage and handling. Ambient conditions may, for example, be a pressure of 900 to 1100 mbar, a temperature of −10 to 60° C. and a relative humidity of 10 to 100%. In the laboratory, ambient conditions are adjusted to 23° C. and 1013 mbar. In the dental and orthodontic field ambient conditions are reasonably understood as a pressure of 950 to 1050 mbar, temperature of 15 to 40° C. and relative humidity of 20 to 80%.

As used herein, "a", "an", "the", "at least one" and "one or more" are used interchangeably. The terms "comprise" or "contain" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

The terms "comprise" or "contain" and variations thereof do not have a limiting meaning where these terms appear in the description and claims. The term "comprise" shall include also the terms "consist essentially of" and "consist of".

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and used in the specification and claims are to be understood as number as such and also as being modified by the term "about."

"And/or" means one or both. E.g., the expression component A and/or component B refers to a component A alone, component B alone, or to both component A and component B.

DETAILED DESCRIPTION

The microcapsules and its use described in the present text are advantageous for a couple of reasons:

The microcapsules contain a porous or hollow core which is suitable to absorb or store active reagents.

The microcapsules further contain a shell or coating which prevents the active reagent to migrate out of the porous or hollow core during storage. Thus, a reaction of the encapsulated components with component(s) surrounding the microcapsule is avoided.

The microcapsules are sufficiently mechanically stable and survive shear forces which typically occur during production process involving a kneading step, e.g. when preparing pasty compositions.

The pH-sensitive shell allows the release of the active reagent from the porous or hollow core on demand, e.g. by bringing the microcapsule in contact with an acidic component.

This can be advantageous for e.g. redox initiator systems contained in dental two-part paste/paste compositions that contain an acidic component.

Thus, the microcapsules described in the present text help to overcome challenges associated e.g. with the production of redox-curable paste/paste compositions.

The pH-sensitive core-shell microcapsule described in the present text comprises a porous or hollow core.

The porous or hollow core is composed of a polymeric material, i.e. a crosslinked matrix. It was found that a crosslinked matrix has sufficient mechanical stability to withstand shear forces which occur during mixing processes.

The microcapsules can typically be characterized by the following features alone or in combination:
a) shape: spherical;
b) diameter: 1 to 200 µm or 1 to 100 µm or 5 to 100 µm or 5 to 50 µm or 5 to 25 µm;
c) pore size of porous core material: 10 to 200 nm or 20 to 200 nm or 50 to 200 nm;
d) mechanically stable.

A combination of the features a) and b) or a) and c) or b) and c) or a), b) and c) or a), b), c) and d) is sometimes preferred.

The shape, diameter and pore size can be evaluated by microscopy, in particular scanning electron microscopy (SEM).

A microcapsule is mechanically stable, if it is able to survive high shear forces, which typically occur during preparing pastes in a kneading machine. A suitable test is described in the example section.

Mechanical stability can be obtained, e.g. if a crosslinked polymeric material, in particular a highly crosslinked polymeric material is used.

The polymeric material of the porous or hollow core is typically a (meth)acrylate, that is, the polymerization product of polymerizable monomers containing (meth)acrylate moieties.

Suitable (meth)acrylates, which may be present in the polymeric material include $$CH_2=C(R^1)-(CO)-O[-CH_2-CH_2-O]_p-(CO)-C(R^1)=CH_2 \quad (1)$$

wherein p is an integer equal to at least 1; $R^1$ is hydrogen or alkyl;

$$CH_2=CR^1-(CO)-O-Y-R^2 \quad (2)$$

wherein $R^1$ is hydrogen or methyl, Y is a single bond, alkylene, oxyalkylene, or poly(oxyalkylene) and $R^2$ is a carbocyclic group or heterocyclic group;
and mixtures thereof.

The term "alkylene" refers to a divalent group that is a radical of an alkane and includes groups that are linear, branched, cyclic, bicyclic or combinations thereof. Suitable alkylene groups are selected from $C_1$ to $C_{20}$ or $C_1$ to $C_{16}$ or $C_1$ to $C_{12}$ or $C_1$ to $C_{10}$ or $C_1$ to $C_8$ or $C_1$ to $C_6$ or $C_1$ to $C_4$ moieties.

The material of the porous or hollow core is typically obtained by emulsion polymerization of suitable monomers. Suitable monomers include those described above.

According to one embodiment, the polymeric material of the porous or hollow core is obtained by polymerizing the components according to formulas (1) and (2) optionally in the presence of other components.

Other components include non-ionic surfactants and/or components of formula (3)

$$HO[-CH_2-CH(OH)-CH_2-O]_n-H \quad (3)$$

wherein n is an integer equal to at least 1.

The polymerization is typically initiated by an initiator for free radical polymerization.

According to a further embodiment, the polymeric material of the porous or hollow core is the polymerized product of a reaction mixture comprising:
a) a first phase comprising
  i) a compound of formula (3); and
  ii) a non-ionic surfactant; and
b) a second phase dispersed in the first phase, wherein the second phase comprises
  iii) a monomer composition comprising a monomer of formula (1);
  iv) a polypropylene glycol, preferably having a Mw of at least 500 g/mol; and
  i) optionally a further monomer of formula (2).

Suitable processes for producing microcapsules having a porous or hollow core are e.g. described in U.S. Pat. No. 9,422,411 B2 (Sahouani et al.) or US 2016/008836 A1 (Sahouani et al.). The content of these references is herewith incorporated by reference. The porous or hollow core contains one component of a redox-initiator system. A redox-initiator system typically comprises oxidizing agent(s) and reducing agent (s). According to one embodiment, the porous or hollow core contains oxidizing agent(s).

The nature and structure of the oxidizing agent(s) is not particularly limited unless the desired result cannot be achieved.

Suitable oxidizing agents include organic and inorganic peroxides, persulfate component(s) and mixtures thereof.

Generally, all peroxide(s), i.e. inorganic and organic peroxides, which can be incorporated or absorbed by the microcapsules can be used.

The oxidizing agent is typically a solid at ambient conditions (23° C.; 1013 hPa). In contrast to inorganic peroxides, organic peroxide(s) do not comprise metals or metal ions. Thus, organic peroxides typically only comprise C, O, H and optionally halogens (e.g. F, Cl, Br).

Organic peroxides which can be used include hydroperoxide(s), ketone peroxide(s), diacyl peroxide(s), dialkyl peroxide(s), peroxyketal(s), peroxyester(s) and peroxydicarbonate(s).

Di-peroxides, which can be used include di-peroxides comprising the moiety $R_1$—O—O—$R_2$—O—O—$R_3$, with $R_1$ and $R_3$ being independently selected from H, alkyl (e.g. $C_1$ to $C_6$), branched alkyl (e.g. $C_1$ to $C_6$), cycloalkyl (e.g. $C_5$ to $C_{10}$), alkylaryl (e.g. $C_7$ to $C_{12}$) or aryl (e.g. $C_6$ to $C_{10}$) and $R_2$ being selected from alkyl (e.g. ($C_1$ to $C_6$) or branched alkyl (e.g. $C_1$ to $C_6$).

Examples of ketone peroxides include methyl ethyl ketone peroxide, methyl isobutyl ketone peroxide, methyl cyclohexanone peroxide,and cyclohexanone peroxide.

Examples of peroxyesters include □-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate and t-butylperoxymaleic acid.

Examples of peroxidicarbonates include di-3-methoxy peroxidicarbonate, di-2-ethylhexyl peroxydicarbonate, bis(4-t-butylcyclohexyl)peroxidicarbonate, diisopropyl-1-peroxydicarbonate, di-n-propyl peroxidicarbonate, di-2-ethoxyethyl-peroxidicarbonate, and diallyl peroxidicarbonate.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxides include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Examples of peroxyketals include 1,1-bi s(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butylester.

According to one embodiment, the organic peroxide is a hydroperoxide, in particular a hydroperoxide comprising the structural moiety R—O—O—H with R being (e.g. $C_1$ to $C_{20}$) alkyl, (e.g. $C_3$ to $C_{20}$) branched alkyl, (e.g. $C_6$ to $C_{12}$) cycloalkyl, (e.g. $C_7$ to $C_{20}$) alkylaryl or (e.g. $C_6$ to $C_{12}$) aryl.

Examples of suitable organic hydroperoxides include t-butyl hydroperoxide, t-amyl hydroperoxide, p-diisopropylbenzene hydroperoxide, cumene hydroperoxide, pinane hydroperoxide, p-methane hydroperoxide and 1,1,3,3-tetramethylbutyl hydroperoxide.

Suitable peroxodisulfate components and/or peroxodiphosphate components and/or mixtures thereof, which can be used include organic and/or inorganic components.

Suitable examples include ammonium, sodium, and potassium peroxodisulfate components and/or peroxodiphosphate components. Sodium peroxodisulfate is sometimes preferred. Alternatively, the hollow or porous core contains reducing agents(s).

The nature and structure of the reducing agent(s) is not particularly limited unless the desired result cannot be achieved.

Suitable reducing agents include organic and inorganic component(s) and mixtures thereof. The reducing agent is typically a solid at ambient conditions (23° C.; 1013 hPa).

Reducing agents (s) which may be contained in the porous or hollow core include ascorbic acid component(s), tertiary amine component(s), sulfinate component(s), sulphite component(s), borane component(s), (thio)urea component(s), and (thio)barbituric acid component(s), saccharin and metal salts thereof.

Component(s) comprising an ascorbic acid moiety such as salts and esters of ascorbic acid, ethers, ketals, or acetals are sometimes preferred.

Suitable salts include the alkali metal and earth alkali metal salts like Na, K, Ca and mixtures thereof.

Esters of ascorbic acid include those, which are formed by reacting one or more of the hydroxyl functions of ascorbic acid with a carboxylic acid, in particular the $C_2$ to $C_{30}$ carboxylic acid.

Suitable examples of $C_2$ to $C_{30}$ carboxylic acids include the fatty acids, like caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

In particular preferred are those ascorbic acid moiety containing components, which can be easily dissolved in or mixed with the remaining resin matrix comprising polymerizable components.

That is, using an ascorbic acid moiety containing component having in addition a hydrophobic moiety can sometimes be preferred. Suitable hydrophobic moieties include saturated and unsaturated aliphatic residues (e.g. $C_2$ to $C_{30}$ or $C_{12}$ to $C_{30}$). Those ascorbic acid derivatives may also function as surface-active substances (substances having a so-called "head/tail structure"). Particularly preferred are sometimes ascorbyl palmitate, ascorbyl stearate, mixtures and salts thereof.

If the oxidizing agents(s) are brought in contact with the reducing agents(s), a redox-reaction typically starts. Such a redox-reaction is suitable to initiate the curing of curable components resulting in the crosslinking of the curable components.

Other components of a redox-initiator system which can be present and be contained in the porous or hollow core include transition metal components.

Suitable transition metal component(s) include organic and/or inorganic salt(s) selected from titanium, vanadium, chromium, manganese, iron, cobalt, nickel, copper and/or zinc, with copper and iron being sometimes preferred.

Useful salts include acetate(s), chloride(s), sulphate(s), benzoate(s), acetylacetonate(s), naphthenate(s), carboxylate(s), bis(1-phenylpentan-1,3-dione) complexes, salicylate(s), complexes with ethylenediamine tetra acetic acid of either of the transition metals and mixtures thereof.

According to one embodiment, the transition metal component is in an oxidation stage, which allows the component to be reduced. Useful oxidation stages include +2, +3, +4, +5, +6 and +7, as applicable.

Copper component(s) are sometimes preferred. The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper salicylate, complexes of copper with thiourea, ethylenediamine tetra acetic acid and/or mixtures thereof. The copper compounds can be used in hydrated form or free of water. Especially preferred is copper acetate.

If desired, the porous or hollow polymer particles can also be filled with other active components, for example a dye(s), or crosslinker(s), fluoride releasing agent(s). Suitable dye(s) and fluoride releasing agent(s) are described in the text below.

The pH-sensitive core-shell microcapsule described in the present text also comprises a shell. The shell covers the porous or hollow core of the microcapsules.

The shell can typically be characterized by the following features alone or in combination:
a) thickness: 0.1 to 5 μm or 0.5 to 4 μm or 1 to 3 μm;
b) coverage: covering at least 85% or at least 90 or at least 95% or at least 99% of the surface of the porous or hollow core;
c) sensitivity: sensitive to or soluble or swellable in acidic or basic components.

The combination of the following features is sometimes preferred: a) and b); a) and c); b) and c); a), b) and c).

If desired, the thickness of the shell can be determined by Scanning Electron Microscopy (SEM), Transmission Electron Microscopy (TEM) or Secondary Ion Mass Spectroscopy (SIMS).

If desired, the extent of coverage of the shell can be determined by Scanning Electron Microscopy (SEM). The shell is composed of a pH-sensitive material.

A pH-sensitive material is a material which dissolves, swells or weakens if brought in contact with another substance which is either a basic or acidic component.

According to one embodiment, the pH-sensitive material is an acid-sensitive material.

Acid-sensitive materials are typically characterized by the following features alone or in combination:
a) dissolving in a composition having a pH in the range of 1 to 6 or of 1 to 4;
b) being stable in composition having a pH in the range of 14 to 7;
c) being polymeric, e.g. having a molecular weight of 10,000 to 1,000,000 g/mol or 20,000 to 500,000 g/mol or 50,000 g/mol to 300,000 g/mol;
d) glass temperature below 200° C. or below 180° C. or below 150° C. or below 100° C.

Examples of acid-sensitive materials include co-polymer(s) of methyl (meth)acrylate and diethylaminoethyl (meth)acrylate (e.g. those sold under the trade name Kollicoat™ Smartseal), co-polymer(s) of methyl (meth)acrylate, butyl methacrylate and dimethylaminoethyl (meth)acrylate (e.g. those sold under the trade name Eudragit™ E), poly(2-(dimethylamino)ethyl methacrylate), cellulose acetate phthalate, sodium carboxymethyl cellulose, hydroxy propyl methyl cellulose phthalate, poly(vinyl acetate phthalate), poly(4-vinyl pyridine), chitosan, and mixtures thereof.

According to another embodiment, the pH-sensitive material is a basic-sensitive material.

Basic-sensitive materials are typically characterized by the following features alone or in combination:
a) dissolving in a composition having a pH in the range of 14 to <7 or of 12 to 8;
b) being stable in composition having a pH in the range of 1 to 7 or in the range of 1 to 5;
c) being polymeric, e.g. having a molecular weight of 10,000 to 1,000,000 g/mol or 20,000 to 500,000 g/mol or 50,000 g/mol to 300,000 g/mol;
d) glass temperature $T_g$: below 200° C. or below 180° C. or below 150° C. or below 100° C.

Examples of basic-sensitive materials include co-polymer(s) of methacrylic acid and methyl (meth)acrylate (e.g. those sold under the trade name Eudragit™ L, S), co-polymer(s) of methacrylic acid and alkyl (e.g. $C_{1-6}$) (meth)acrylate, co-polymer(s) of methacrylic acid, methyl (meth)acrylate and methyl acrylate (e.g. those sold under the trade name Eudragit™ FS 30D), poly(acrylic acid), poly(sulfonic acid), poly(styrene sulfonic acid, poly(2-hydroxylethyl methacrylate) phosphate, hyaluronic acid, and mixtures thereof.

The pH-sensitive microcapsule described in the present text can be produced as follows:

Porous or hollow particles and component(s) of a redox-initiator system as described in the present text are provided.

The porous or hollow particle are treated with the component(s) of a redox-initiator system in a manner enabling the porous particles to absorb the component(s) of a redox-initiator system.

If the component(s) of a redox-initiator system are in a solid or high viscous state, the component(s) are typically dissolved in a solvent first.

After the treatment, the solvent is typically evaporated, e.g. by drying the treated microcapsules.

Suitable solvents include water and low-boiling solvents. Low-boiling solvents typically have a boiling point at ambient pressure below 80° C.

Suitable solvents include water, methylene chloride, low boiling ethers (e.g. tetrahydrofuran, methyl tert. butyl ether), alcohols (e.g. methanol, ethanol, iso- and n-propanol), and mixtures thereof.

After the treatment, the component(s) of a redox-initiator system are located in or absorbed by the pores of the porous particles.

If desired, the treating process can be characterized by the following features, alone or in combination:
a) duration: 5 to 60 min;
b) temperature: 20 to 60° C.;
c) pressure: ambient pressure
d) stirring the mixture.

The combination of the following features is sometimes preferred: a) and b); a), b) and c); or a), b), c) and d).

The porous or hollow particles having the component(s) of the redox-initiator system contained in the pores is then treated with a pH-sensitive coating agent.

Examples of pH-sensitive coating agents include those mentioned above.

If desired, the coating process can be characterized by the following features, alone or in combination:
a) the coating process being done by spray-drying;
b) duration: 0.1 to 10 h, or 0.2 to 5 h;
c) temperature: 20 to 90° C. or 30 to 80° C. or 40 to 70° C.;
d) pressure: ambient pressure (e.g. 900 to 1030 hPa).

The combination of the following features is sometimes preferred: b) and c); or a), b) and c); or a), b), c) and d).

The spray drying is typically done at a temperature around the $T_g$ (glass temperature) of the polymer.

It has been found that this temperature is often appropriate to ensure an appropriate encapsulation and to obtain a smooth and homogenous surface.

Thus, typical coating agents are polymers, copolymers or waxes with glass transition temperatures ($T_g$) below 200° C. and a molecular weight (Mw) in the range of 20,000 to 500,000 g/mol.

The spray drying is typically performed at temperatures around the $T_g$ of the coating agent. This may help to achieve a successful encapsulation and fabrication of a smooth and homogenous surface.

The invention also relates to a kit of parts. The kit of parts comprises a Catalyst Paste and a Base Paste.

The Catalyst Paste comprises pH-sensitive core-shell microcapsule(s) as described in the present text, which comprises a first component of a redox-initiator system.

The Base Paste comprises an acidic or basic component and a second component of the redox-initiator system.

The first and second component of the redox-initiator system together form an initiator system which is suitable to initiate the curing of curable components being present in the Catalyst Paste or the Base Paste or in the Catalyst Paste and the Base Paste.

According to one embodiment, the first component of a redox-initiator system contained in the pH-sensitive microcapsules is a reducing agent and the second component of the redox-initiator system is an oxidizing agent.

According to another embodiment, the first component of a redox-initiator system contained in the pH-sensitive microcapsules is an oxidizing agent and the second component of the redox-initiator system is a reducing agent.

The oxidizing and reducing agents include those described above.

According to one embodiment, the kit of parts comprises two kinds of microcapsules, microcapsules containing a reducing agent and microcapsules containing an oxidizing agent.

The shell of these microcapsules is composed of either an acid-sensitive or a basic-sensitive material, preferably by an acid-sensitive material. According to one embodiment, the Base Paste contains an acidic component.

The acid component contained in the Base Paste is a component being suitable to interact with the pH-sensitive shell of the microcapsule, such that the pH-sensitive shell is weakened (e.g. dissolved) enabling the first component of the redox-initiator system to migrate out of the pores of the porous core.

The nature and structure of these components is not particularly limited unless the intended purpose cannot be achieved. Inorganic and organic acidic components can be used, as desired.

Inorganic acidic components which can be used include hydrochloric acid, sulfuric acid, phosphoric acid, mixtures thereof and its acidic salts.

Organic acidic components which can be used include monocarboxylic acids such as formic acid, acetic acid and benzoic acid and derivatives of these acids or dicarboxylic acids chosen from oxalic acid, malonic acid, succinic acid, adipic acid, pimelic acid, azelaic acid, sebacic acid, maleic acid, fumaric acid, sorbic acid, phthalic acid and terephthalic acid and derivatives of these acids or tricarboxylic acids chosen from hemimellitic acid, trimellitic acid, trimesic acid, agaric acid, citric acid, 1,2,3-propanetricarboxylic acid and derivatives of these acids or multicarboxylic acids chosen from the group consisting of pyromellitic acid and mellitic acid and derivatives of these acids or polycarboxylic acids chosen from polyacrylic acid and polymethacrylic acid and derivatives of these acids and mixtures thereof.

The acidic component can be characterized by the following features alone or in combination:
a) pKs value: equal to or below 5, equal to or below 4 or equal to or below 3.5 or equal to or below 3 or equal to or below 2;
b) comprising acidic moieties selected from sulfonic, sulfinic, phosphoric, phosphonic, phosphinic, or carboxylic moieties.

If desired, the acidic component may also comprise one or more polymerizable moieties, such as (meth)acrylate moieties. One or more polymerizable component(s) with acidic moiety(s) may be present, if desired.

The polymerizabel components with acid moiety can typically be represented by the following formula

$A_n BC_m$ with A being an ethylenically unsaturated group, such as a (meth)acryl moiety, B being a spacer group, such as (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), (iii) organic group having 4 to 20 carbon atoms bonded to one another by one or more ether, thioether, ester, thioester, thiocarbonyl, amide, urethane, carbonyl and/or sulfonyl linkages, and C being an acidic group, or precursor of an acidic group such as acid anhydride, m, n being independently selected from 1, 2, 3, 4, 5 or 6, wherein the acidic group comprises one or more carboxylic acid residues, such as —COOH— or —CO—O—CO—, phosphoric acid residues, such as —O—P(O)(OH)OH, phosphonic acid residues, such as C—P(O)(OH)(OH), sulfonic acid residues, such as —$SO_3$H or sulfinic acid residues such as —$SO_2$H.

Examples of polymerizable components with acid moiety include, but are not limited to glycerol phosphate mono (meth)acrylate, glycerol phosphate di(meth)acrylate, hydroxyethyl (meth)acrylate (e.g., HEMA) phosphate, bis((meth)acryloxyethyl) phosphate, (meth)acryloxypropyl phosphate, bis((meth)acryloxypropyl) phosphate, bi s((meth)acryloxy)propyloxy phosphate, (meth)acryloxyhexyl phosphate, bi s((meth)acryloxyhexyl) phosphate, (meth)acryloxyoctyl phosphate, bi s((meth)acryloxyoctyl) phosphate, (meth)acryloxydecyl phosphate, bis((meth)acryloxydecyl) phosphate, caprolactone methacrylate phosphate, citric acid di- or tri-methacrylate, poly(meth)acrylated oligomaleic acid, poly(meth)acrylated polymaleic acid, poly (meth)acrylated poly(meth)acrylic acid, poly(meth)acrylated polycarboxyl-polyphosphonic acid, poly(meth) acrylated polychlorophosphoric acid, poly(meth)acrylated polysulfonate, poly(meth)acrylated polyboric acid, and the like. Derivatives of these hardenable components bearing an acid moiety that can readily react e.g. with water to form the specific examples mentioned above, like acid halides or anhydrides are also contemplated.

Also, monomers, oligomers, and polymers of unsaturated carboxylic acids such as (meth)acrylic acids, aromatic (meth)acrylated acids (e.g., methacrylated trimellitic acids), and anhydrides thereof can be used.

If present, the acidic component(s) are typically present in the following amounts:
Lower amount: at least 2 or at least 3 or at least 4 wt. %;
Upper amount: utmost 50 or utmost 40 or utmost 30 wt. %;
Range: 2 to 50 or 3 to 40 or 4 to 30 wt. %;

wt. % with respect to the weight of the composition obtained by mixing the Catalyst Paste and Base Paste of the kit of parts. According to another embodiment, the Base Paste contains a basic component.

The basic component contained in the Base Paste is a component being suitable to interact with the pH-sensitive shell of the microcapsule, such that the pH-sensitive shell is weakened (e.g. dissolved) enabling the first component of the redox-initiator system to migrate out of the pores of the porous core.

The nature and structure of these components is not particularly limited unless the intended purpose cannot be achieved. Inorganic and organic basic components can be used, as desired.

Inorganic basic components which can be used include the salts of hydroxide(s), carbonate(s), phosphate(s) (including sodium, potassium, calcium and ammonium salts) and the aqueous solutions thereof. Also included are inorganic alkaline glasses such as fluoroaluminosilicate glasses (acid-reactive glasses).

Organic basic components include primary, secondary and tertiary aliphatic (e.g. $C_2$ to $C_6$ alkyl) amines, and mixtures thereof.

If present, the basic component(s) are typically present in the following amounts:
Lower amount: at least 1 or at least 3 or at least 5 wt. %;
Upper amount: utmost 70 or utmost 60 or utmost 50 wt. %;
Range: 1 to 70 or 3 to 60 or 5 to 50 wt. %;
wt. % with respect to the weight of the composition obtained by mixing the Catalyst Paste and Base Paste of the kit of parts.

The curable component(s) which are typically contained in pastes of the kit of parts are components which can be polymerized in the presence of the redox-initiator system. According to one embodiment, the curable component(s) do not contain an acidic moiety.

One or more polymerizable component(s) without acidic moiety(s) may be present, if desired.

The nature and structure of those components is not particularly limited unless the intended purpose cannot be achieved.

The polymerizable component(s) without acidic moiety (s) is typically a free-radically polymerizable material, including ethylenically unsaturated monomer, monomers or oligomers or polymers.

Suitable polymerizable component(s) without acidic moiety(s) can be characterized by the following formula:

$$A_n BA_m$$

with A being an ethylenically unsaturated group, such as a (meth)acryl moiety, B being selected from (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Rohm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycoldi(meth)acrylate, diethyleneglycoldi (meth)acrylate, triethyleneglycoldi(meth)acrylate, 1,3-propanedioldiacrylate, 1,3-propanediol dimethacrylate, trimethylolpropane tri(meth)acrylate, 1,2,4-butanetriol tri (meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-acryloxy-2-hydroxy)]-p-propoxy-phenyldimethylmethane and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components which may be present include di(meth)acrylates of ethoxylated bis-phenol A, for example 2,2'-bis(4-(meth)acryl-oxytetraethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3[4]-methacryl-oxymethyl-8 (9)-tricyclo[$5.2.1.0^{2,6}$]decylmethyl triglycolate. Suitable are also 2,2-bis-4(3-methacryloxy-2-hydroxypropoxy)phenylpropane (Bis-GMA), 2,2-bis-4(3 -methacryloxypropoxy) phenylpropane, 7,7,9-trimethyl-4,13-dioxo-3,14-dioxa-5, 12-diazahexadecane-1,16-dioxy dimethacrylate (UDMA), urethane (meth)acrylates and di(meth)acrylates of bishydroxymethyltricyclo-($5.2.1.0^{2,6}$)decane.

These ethylenically unsaturated monomers can be employed in the dental composition(s) either alone or in combination with the other ethylenically unsaturated monomers. In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

The curable component(s) without acidic moieties are typically present in the following amounts:
Lower amount: at least 5 or at least 10 or at least 20 wt. %;
Upper amount: utmost 65 or utmost 55 or utmost 45 wt. %;
Range: 5 to 65 or 10 to 55 or 20 to 45 wt. %;
wt. % with respect to the weight of the composition obtained by mixing the Catalyst Paste and Base Paste of the kit of parts.

The Catalyst Paste and/or the Base Paste may contain further components, including filler(s), photo initiator(s) and additives including fluoride release agent(s), stabilizer(s), colorant(s).

The amounts and types of each ingredient in the composition should be adjusted to provide the desired physical and handling properties before and after polymerization.

One or more fillers may be present, if desired. The nature and structure of the filler(s) is not particularly limited unless the intended purpose cannot be achieved.

Adding a filler can be beneficial e.g. for adjusting the rheological properties like the viscosity. The content of the filler also typically influences the physical properties of the composition after hardening, like hardness or flexural strength.

The size of the filler particles should be such that a homogeneous mixture with the hardenable component forming the resin matrix can be obtained. The mean particle size of the filler may be in the range from 5 nm to 100 µm.

If desired, the measurement of the particle size of the filler particles can be done with a TEM (transmission electron microscopy) method, whereby a population is analysed to obtain an average particle diameter.

A preferred method for measuring the particle diameter can be described as follows: Samples approximately 80 nm thick are placed on 200 mesh copper grids with carbon stabilized formvar substrates (SPI Supplies- a division of Structure Probe, Inc., West Chester, PA). A transmission electron microscopy (TEM) is taken, using JEOL™ 200CX (JEOL, Ltd. of Akishima, Japan and sold by JEOL USA, Inc.) at 200 Kv. A population size of about 50-100 particles can be measured and an average diameter is determined.

The filler(s) typically comprise non acid-reactive fillers. A non-acid reactive filler is a filler which does not undergo an acid/base reaction with an acid.

Useful non-acid reactive fillers include fumed silica, fillers based on non-acid reactive fluoroaluminosilicate glasses, quartz, ground glasses, non water-soluble fluorides such as $CaF_2$, silica gels such as silicic acid, in particular pyrogenic silicic acid and granulates thereof, cristobalite, calcium silicate, zirconium silicate, zeolites, including the molecular sieves.

Suitable fumed silicas include for example, products sold under the tradename Aerosil™ series OX-50, -130, -150, and -200, Aerosil™ R8200, -R805 available from Degussa AG (Hanau, Germany), CAB-O-SIL™ M5 available from Cabot Corp (Tuscola, Ill.), and HDK types e.g. HDK™-H2000, HDK™ H15, HDK™ H18, HDK™ H20 and HDK™ H30 available from Wacker.

Filler(s) which can also be used and which provide radiopacity to the dental materials described in the present text include heavy metal oxide(s) and fluoride(s). As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling.

Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. yttrium trifluoride and ytterbium trifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than 200 nm, and more preferably are less than 90 nm in average diameter.

Other suitable fillers to increase radiopacity are salts of barium and strontium especially strontium sulphate and barium sulphate.

Filler(s) which can also be used include nano-sized fillers such as nano-sized silica.

Suitable nano-sized particles typically have a mean particle size in the range of 5 to 80 nm.

Preferred nano-sized silicas are commercially available from Nalco Chemical Co. (Naperville, Ill.) under the product designation NALCO™ COLLOIDAL SILICAS (for example, preferred silica particles can be obtained from using NALCO™ products 1040, 1042, 1050, 1060, 2327 and 2329), Nissan Chemical America Company, Houston, Texas (for example, SNOWTEX-ZL, -OL, -O, -N, -C, -20L, -40, and -50); Admatechs Co., Ltd., Japan (for example, SX009-MIE, SX009-MIF, SC1050-MJM, and SC1050-MLV); Grace GmbH & Co. KG, Worms, Germany (for example, those available under the product designation LUDOX™, e.g., P-W50, P-W30, P-X30, P-T40 and P-T4OAS); Akzo Nobel Chemicals GmbH, Leverkusen, Germany (for example, those available under the product designation LEVASIL™, e.g., 50/50%, 100/45%, 200/30%, 200A/30%, 200/40%, 200A/40%, 300/30% and 500/15%), and Bayer MaterialScience AG, Leverkusen, Germany (for example, those available under the product designation DISPERCOLL™ S, e.g., 5005, 4510, 4020 and 3030).

Surface-treating the nano-sized silica particles before loading into the dental material can provide a more stable dispersion in the resin. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

Thus, the silica particles as well as other suitable non acid-reactive fillers can be treated with a resin-compatibilizing surface treatment agent.

If present the filler(s) are typically present in the following amounts:
  Lower amount: at least 1 or at least 5 or at least 10 wt. %;
  Upper amount: utmost 80 or utmost 70 or utmost 60 wt. %;
  Range: 1 to 80 or 5 to 70 or 10 to 60 wt. %;
wt. % with respect to the weight of the composition obtained by mixing the Catalyst Paste and Base Paste of the kit of parts.

The kit of parts may also include photo initiator(s).

The nature and structure of the photo initiator is not particularly limited unless the intended purpose is not negatively affected. Suitable photo initiator(s) for free radical polymerization are generally known to the person skilled in the art dealing with dental materials.

As photo initiator(s), those which can polymerize the polymerizable monomer(s) by the action of visible light having a wavelength of from 350 nm to 500 nm are preferred. Suitable photo initiator(s) often contain an alpha di-keto moiety, an anthraquinone moiety, a thioxanthone moiety or benzoin moiety.

Examples of photo initiator(s) include camphorquinone, 1-phenyl propane-1,2-dione, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthra-quinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluorom ethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

Using acylphosphine oxides was found to be useful, as well.

Suitable acylphosphine oxides can be characterized by the following formula

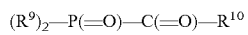

$(R^9)_2$—P(=O)—C(=O)—$R^{10}$ wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having 2 to 6 carbon atoms.

Suitable systems are also described e.g. in U.S. Pat. No. 4,737,593 (Ellrich et al.), the content of which is herewith incorporated by reference.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. In particular, 2,4,6-trimethylbenzoyl diphenyl phosphine oxide was found to be useful (Lucirin™ TPO, BASF).

Suitable bisacylphosphine oxides can also be described by the following formula:

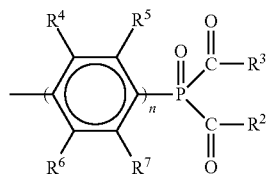

wherein n is 1 or 2, and $R^4$, $R^5$, $R^6$ and $R^7$ are H, $C_{1-4}$ alkyl, $C_{1-4}$ alkoxyl, F, Cl or Br; $R^2$ and $R^3$, which are the same or different, stand for a cyclohexyl, cyclopentyl, phenyl, naphthyl, or biphenylyl radical, a cyclopentyl, cyclohexyl, phenyl, naphthyl, or biphenylyl radical substituted by F, Cl, Br, I, C1-4 alkyl and/or $C_{1-4}$ alkoxyl, or an S or N-containing 5-membered or 6-membered heterocyclic ring; or $R^2$ and $R^3$ are joined to form a ring containing from 4 to 10 carbon atoms and being optionally substituted by 1 to 6 $C_{1-4}$ alkyl radicals.

More specific examples include: bis-(2,6-dichlorobenzoyl)phenylphosphine oxide, bi s-(2,6-dichlorobenzoyl)-2, 5 -dimethylphosphine oxide, bi s-(2,6-dichlorobenzoyl)-4-ethoxyphenylphosphine oxide, bis-(2,6-dichlorobenzoyl)-4-biphenylylphosphine oxide, bis-(2,6-dichlorobenzoyl)-4-propylphenylphosphine oxide, bis-(2,6-dichlorobenzoyl)-2-naphthylphosphine oxide, bis-(2,6-dichlorobenzoyl)-1-napthylphosphine oxide, bis-(2,6-dichlorobenzoyl)-4-chlorophenylphosphine oxide, bis-(2,6-dichlorobenzoyl)-2,4-dimethoxyphenylphosphine oxide, bis-(2,6-dichlorobenzoyl)decylphosphine oxide, bis-(2,6-dichlorobenzoyl)-4-octylphenylphosphine oxide, bis-(2,6-dimethoxybenzoyl)-2,5-dimethylphenylphosphine oxide, bis-(2,6-dimethoxybenzoyl)phenylphosphine oxide, bis-(2,4,6-trimethylbenzoyl)-2,5-dimethylphenylphosphine oxide, bis-(2,6-dichloro-3,4,5-trimethoxybenzoyl)-2,5-dimethylphenylphosphine oxide, bis-(2,6-dichloro-3,4,5-trimethoxybenzoyl)-4-ethoxyphenylphosphine oxide, bis-(2-methyl-1-naphthoyl)-2,5-dimethylphenylphosphine oxide, bis-(2-methyl-1-naphthoyl)phenylphosphine oxide, bis-(2-methyl-1-naphthoyl)-4-biphenylylphosphine oxide, bis-(2-methyl-1-naphthoyl)-4-ethoxyphenylphosphine oxide, bis-(2-methyl-1-naphthoyl)-2-naphthylphosphine oxide, bis-(2-methyl-1-naphthoyl)-4-propylphenylphosphine oxide, bis-(2-methyl-1-naphthoyl)-2,5-dimethylphosphine oxide, bis-(2-methoxy-1-naphthoyl)-4-ethoxyphenylphosphine oxide, bis-(2-methoxy-1-naphthoyl)-4-biphenylylphosphine oxide, bis-(2-methoxy-1-naphthoyl)-2-naphthylphosphine oxide and bis-(2-chloro-1-naphthoyl)-2,5-dimethylphenylphosphine oxide.

The acylphosphine oxide bis(2,4,6-trimethylbenzoyl)phenyl phosphine oxide (previously known as IRGACURE™ 819, Ciba Specialty Chemicals) is sometimes preferred.

If present, the photo initiator is typically present in the following amounts:

Lower amount: at least 0.1 or at least 0.2 or at least 0.3 wt. %;

Upper amount: up to 10 or up to 8 or up to 6 wt. %;

Range: 0.1 to 10 or 0.2 to 8 or 0.3 to 6 wt. %;

wt. % with respect to the weight of the composition obtained by mixing the Catalyst Paste and Base Paste of the kit of parts.

Examples of dyes or pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725.

Examples of fluoride release agents which can be present include naturally occuring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, and phenothiazine.

Further additives, which can be added, include retarder(s), (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), and flavorant(s).

There is no need for these adjuvants or additives to be present, so adjuvants or additives might not be present at all. However, if they are present they are typically present in an amount which is not detrimental to the intended purpose.

If present, additive(s) is (are) typically present in the following amounts.

Lower amount: at least 0.01 wt. % or at least 0.05 wt. % or at least 0.1 wt. %;

Upper amount: utmost 15 wt. % or utmost 10 wt. % or utmost 5 wt. %;

Range: 0.01 wt. % to 15 wt. % or 0.05 wt. % to 10 wt. % or 0.1 wt. % to 5 wt. %.

The amount is given with respect to the weight of the whole composition obtained when combining the Catalyst Paste and the Base Paste.

The Catalyst Paste and the Base Paste of the kit of parts are typically stored in a packaging device during storage.

The Catalyst Paste and the Base Paste of the kit of parts described in the present text may be contained in separate sealable vessels (e.g. made out of plastic or glass).

For use, the practitioner may take adequate portions of the compositions contained from the vessels and mix the portions by hand on a mixing plate.

According to a preferred embodiment, the Catalyst Paste and the Base Paste are contained in separate compartments of a storing device.

The storing device typically comprises two compartments for storing the respective parts, each compartment being equipped with a nozzle for delivering the respective part. Once delivered in adequate portions, the parts can then be mixed by hand on a mixing plate.

According to another preferred embodiment, the storing device has an interface for receiving a static mixing tip. The mixing tip is used for mixing the respective pastes. Static mixing tips are commercially available e.g. from Sulzer-Mixpac company. Suitable storing devices include cartridges, syringes and tubes.

The storing device typically comprises two housings or compartments having a front end with a nozzle and a rear end and at least one piston movable in the housing or compartment.

Cartridges which can be used are described e.g. in US 2007/0090079 or U.S. Pat. No. 5,918,772, the disclosure of which is incorporated by reference. Some of the cartridges which can be used are commercially available e.g. from Sulzer Mixpac AG (Switzerland). Static mixing tips which can be used are described e.g. in US 2006/0187752 or in U.S. Pat. No. 5,944,419, the disclosure of which is incorporated by reference. Mixing tips which can be used are commercially available from Sulzer Mixpac AG (Switzerland), as well.

Other suitable storing devices are described e.g. in WO 2010/123800 (3M), WO 2005/016783 (3M), WO 2007/104037 (3M), WO 2009/061884 (3M), in particular the device shown in FIG. 14 of WO 2009/061884 (3M) or WO 2015/073246 (3M), in particular the device shown in FIG. 1 of WO 2015/07346. Those storing devices have the shape of a syringe. The content of these references is herewith incorporated by reference, as well.

Alternatively, but less preferred, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing the Catalyst Paste and Compartment B containing the Base Paste, the Catalyst Paste and the Base Paste being as described in the present text, Compartment A and Compartment B both comprising a nozzle or an interface for receiving an entrance orifice of a static mixing tip.

The mixing ratio of the Base Paste and the Catalyst Base Paste is typically 3:1 to 1:3 with respect to volume, preferably 2:1 to 1:2, more preferably 1:1.

The pH-sensitive microcapsule described in the present text is particularly useful for producing a curable composition comprising a redox-initiator system.

According to one embodiment, the curable composition is a dental or orthodontic composition.

According to one embodiment, the curable composition is a dental or orthodontic cement, adhesive or filing material.

The pH-sensitive microcapsule described in the present text are particularly useful for producing a curable composition obtained by combining two pastes, a base paste and a catalyst paste, wherein one of the pastes contain the pH-sensitive microcapsules described in the present text and the other paste contains an acidic component.

When mixing the two pastes, the paste containing the acidic component comes in contact with the pH-sensitive shell of the pH-sensitive microcapsules. Upon contact, the pH-sensitive shell is dissolved. This enables the component of the redox-initiator system to migrate out of the porous core. Self-adhesive dental materials usually contain an acidic paste.

The acidity of this paste can be used as trigger to remove the shell from the microcapsule upon mixing of both pastes thereby releasing the encapsulated component or agent, in particular, the component of a redox-initiator system. The invention also relates to a process of curing a curable composition.

Such a process comprises the following steps:

A Catalyst Paste comprising the pH-sensitive microcapsules described in the present text and a Base Paste comprising an acidic or basic component is provided.

Either the Catalyst Paste or the Base Paste or the Catalyst Paste and the Base Paste comprise curable components and a further component of a redox-initiator system.

The Catalyst Paste and the Base Paste are mixed.

The acidic component contained in the Base Paste dissolves or weakens the pH-sensitive shell of the microcapsule resulting in a release of the redox-initiator component contained therein.

If brought in contact with each other, the redox-initiator components initiate the curing of the curable components of the curable composition.

According to one embodiment, the kit of parts is characterized as follows:

the Catalyst Paste comprising:
  the pH-sensitive microcapsules as described in the present text comprising a reducing component, preferably a component comprising an ascorbic acid moiety,
  curable non-acidic (meth)acrylate component(s),
  filler(s), the Base Paste B comprising:
  acidic component(s), preferably a polymerizable component comprising an acidic moiety,
  curable (meth)acrylate component(s),
  filler(s),
  oxidizing component,
  the reducing component and the oxidizing agent forming a redox-initiator system for curing the curable (meth)acrylate component(s).

According to another embodiment, the kit of parts is characterized as follows:
the Catalyst Paste comprising:
  the pH-sensitive microcapsules as described in the present text comprising an oxidizing component, preferably a component comprising a peroxide moiety,
  curable non-acidic (meth)acrylate component(s),
  filler(s),
the Base Paste B comprising:
  acidic component(s), preferably a polymerizable component comprising an acidic moiety,
  curable (meth)acrylate component(s),
  filler(s),
  reducing component,
  the reducing component and the oxidizing agent forming a redox-initiator system for curing the curable (meth)acrylate component(s).

The shell of the pH-sensitive microcapsules is typically an acidic-sensitive material, including those described above.

The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Materials

TABLE 1

| Compound | Abbreviation |
| --- | --- |
| Triethylene glycol dimethacrylate | TEGDMA |
| Diurethane dimethacrylate | UDMA |
| Hydroxyethyl methacrylate | HEMA |
| 1,3-glycerol dimethacrylate phosphate | GDM-P |
| De-ionized water | $H_2O$ |
| Glass powder G018-163 (Schott), 2.5% silanized (filler) | GP |
| Fumed silica (rheological additive) | Silica |
| Phosphite (stabilizer) | STAB |
| butylated hydroxytoluene (stabilizer) | BHT |
| Irgacure ™ 819 (photoinitiator) | IC 819 |
| BHT, Cu(Ac)$_2$ in GDM-P | Solution 1 |
| Tert. amyl hydroperoxide (oxidizing agent) | AHP |
| Ascorbic acid derivative (reducing agent) | AAD |
| Amine hydrochloride; 2 wt. % in TEGDMA (accelerator) | ACL |
| Solvent Blue 35 | Sudan II |
| Kollicoat ™ Smartseal 30D (coating agent) | |
| Eudragit ™ EPO (coating agent) | |

Methods

Viscosity

If desired, the viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 μm. The shear rate is ramped down logarithmically from 100 $s^{-1}$ to 0.001 $s^{-1}$.

Measurement of Colour Values (L*a*b* Colour Coordinates)

The device is calibrated using white and black background as reference. The specimens are placed in front of the irradiation. Then, the L*a*b* colour coordinates as well as the contrast ratio (opacity) are determined. Positive b*-values indicate a yellow color, whereas negative b*-values indicate a blue color.

Scanning Electron Microscopy (SEM)

If desired, the coating process of the microcapsules can be further analysed by SEM, e.g. using the device JSM 5400 (Hitachi).

Mechanical Stability

If desired, the mechanical stability of the microcapsules can be determined as follows:

The microcapsules to be analysed are filled with Sudan blue II (a dye having a blue color)—as described below. The filled microcapsules are then coated with a coating agent. Pastes are then prepared using e.g. the following composition: 18 wt. % TEGDMA, 20 wt. % UDMA, 52.02 wt. % glass filler, 8.0 wt. % fumed silica, 0.1 wt. % IC 819, 0.46 wt. % coated filled microcapsules.

The composition is mixed by using a commercially available speedmixer (e.g. SpeedMixer™ DAC 150 SP; Hauschild, Germany) applying the following conditions: 3× 90 s, 2500 RPM and 3× 20 s 3500 RPM with cooling to room temperature after each mixing step.

From this composition light-cured discs are prepared: 700 mg of the paste is filled into a cylindrical mold (15 mm diameter; 1.5 mm height) which is placed between glass slides covered with transparency films. This sandwich-like structure is irradiated from both sides for 20s (without light guide) using an Elipar™ S10 light curing device (3M Oral Care).

Then, the specimen is removed from the mold and put into a Visio™ Beta Vario light oven with vacuum (3M Oral Care) for 7 min to fully light cure the sample.

Then, the L*a*b* color coordinates are determined. If the b* value is positive, the blue color Sudan Blue II obviously did not release from the microcapsules during the paste and disc preparation. This is an indication that the tested microcapsules are mechanically stable. If the b* value is negative, the blue color Sudan Blue II obviously did release from the microcapsules during the paste and disc preparation. This is an indication that the tested microcapsules are mechanically not stable.

A Prove of Principle

The blue dye Sudan II was used as a model substance, because its release from microcapsules can easily be tracked visually or by color measurements.

A1 Preparation of Porous Microcapsules

The monomers SR 339 (100 grams) and SR 603OP (100 grams) obtained from Sartomer and sulfo-ethyl-methacrylate (10 grams) were mixed with Acclaim™ Polyol PPG 4200 (86 grams) from Covestro and IRGACURE™ 819 (600 milligrams). The mixture was stirred vigorously for 20 min. This mixture was then added to 1,200 grams of glycerol previously mixed with 36 g of the surfactant APG 325 from Cognis Corporation. The mixture was shear mixed for 10 min with a high shear mixer. The mixture was then spread thin between to sheets of polyethylene terephthalate (PET) and cured with long wavelength UVA for 15 minutes with a light intensity of 5 mW/cm$^2$. The cured mixture was then dispersed in four bottles in isopropyl alcohol (300 mL) and centrifuged at 3,000 rpm. The supernatant was removed and the resulting particles were then re-suspended in four bottles with 500 mL of isopropyl alcohol for a second rinse followed by centrifugation. After this, the particles were suspended in 4 bottles containing 300 mL isopropyl alcohol and shaken for 2 min and centrifuged again. This extracted the PPG and left pores in the particles. (FIGS. 1A, 2A). These microcapsules are designated as MC1.

A2 Filling of Porous Microcapsules With Sudan II 4 g Silquest™ A 187 were mixed with 0.1 g of Sudan II. This liquid mixture was added to 20 g of the porous microcapsules MC1 and rolled in a glass container for 2 h. The microcapsules absorbed the active agent and kept the active agent inside (FIG. 1B). The obtained microcapsules are designated as MC1-SD-C0.

A3 Coating of Porous and Filled Microcapsules With a pH-sensitive Polymer

The filled porous microcapsules MC1-SD-C0 were coated with a shell via spray drying. The spray drying was done with a spray drier from Büchi, Type B 290 with an inlet temperature range of 55° C. to 60° C. The experiments were performed with the following coating agent:

Microcapsules filled with Sudan II and coated with Kollicoat™ Smartseal 30 D are designated as MC1-SD-C1. Non-coated microcapsules filled with Sudan II are designated as MC 1-SD-C0.

Microcapsule containing a dye as active reagent and coated with a pH-sensitive shell are shown in FIG. 1C.

B Paste Compositions

Pastes A1 and A2

Pastes A1 and A2 were prepared by weighing in the respective compounds. Different weight percentages of MC1-SD-C0 and MC1-SD-C1 were weighed in to obtain the same amount of Sudan II in both pastes A1 and A2 for better comparison. The mixture was mixed by using a commercially available SpeedMixer™ DAC 150 SP (Hauschild, Germany) by application of 3× 90 s, 2500 RPM and 3× 20 s 3500 RPM (cooling to room temperature after each mixing step).

TABLE 2

| Compound | Paste A1 Amount [wt. %] | Paste A2 Amount [wt. %] |
| --- | --- | --- |
| TEGDMA | 16.00 | 16.00 |
| UDMA | 20.00 | 20.00 |
| GP | 52.02 | 52.38 |
| Silica | 8.00 | 8.00 |
| MC1-SD-C0 | — | 0.10 |
| MC1-SD-C1 | 0.46 | — |
| AAD | 0.92 | 0.92 |
| STAB | 0.50 | 0.50 |
| ACL | 2.00 | 2.00 |
| IC 819 | 0.10 | 0.10 |

Paste B

Paste B1 was prepared by weighing in the respective compounds. Then, the mixture was mixed by using a commercially available SpeedMixer™ DAC 150 SP (Hauschild, Germany) by application of 3× 90 s, 2500 RPM and 2× 60 s 3500 RPM (cooling to room temperature after each mixing step).

TABLE 3

| Compound | Paste B1 Amount [wt. %] |
| --- | --- |
| HEMA | 20.0 |
| GDM-P | 15.0 |
| H$_2$O | 10.0 |
| Silica | 46.7 |
| Solution 1 | 6.0 |
| AHP | 2.3 |

B1 Preparation of Light-cured Specimens of Paste A1 and A2

700 mg of Paste Ax was filled into a cylindrical mould (15 mm diameter; 1.5 mm height) which was placed between glass slides covered with transparency films. This sandwich-like structure was irradiated from both sides for 20s (without light guide) using an Elipar™ S10 light curing device (3M Oral Care). Then, the specimen was removed from the mould and put into a Visio™ Beta Vario light oven with vacuum (3M Oral Care) for 7 min to fully light cure the sample and remove the inhibition layer.

The cured samples were further analysed with respect to their colour values. The results are given below (Table 4).

TABLE 4

| Paste | Capsule Code | L* | a* | b* | Opacity | Visual Appearance |
| --- | --- | --- | --- | --- | --- | --- |
| A1 | MC-SD-C1 | 74.3 | −3.6 | 3.7 | 24.7 | slightly yellow |
| A2 | MC-SD-C0 | 70.4 | −7.8 | −3.2 | 27.4 | blue |

Although both pastes A1 and A2 contain the same amount of the dye Sudan II, there is a difference in terms of their b*-values and appearance. Paste A1 had a b*-value of 3.7 and appeared slightly yellow, whereas paste A2 had a b*-value of −3.2 and appeared blue.

Apparently, the coating of the porous, Sudan II containing core survives the speed mixing process and delivers uniformly sealed coated microcapsules as confirmed by SEM pictures (FIG. 1C).

B2 Preparation of Light-cured Specimens of Paste A1-A2 and B1

420 mg of Paste Ax was hand mixed with 300 mg of Paste B1 (mixing ratio 1.4: 1.0) for 30s on a mixing pad with the help of a spatula. Then, the mixture was filled into a cylindrical mould (15 mm diameter; 1.5 mm height) which was placed between glass slides covered with transparency films. This sandwich-like structure was irradiated from both sides for 20s (without light guide) using an Elipar™ S10 light curing device (3M Oral Care). Then, the specimen was removed from the mould and put into a Visio™ Beta Vario light oven with vacuum (3M Oral Care) for 7 min to fully light cure the sample and remove the inhibition layer.

The specimens of Example 1 and 2 were prepared by mixing and light curing the Paste A1-A2 with Paste B1 as described below.

TABLE 5

| Ex. | Capsule Code | Paste | Paste | L* | a* | b* | Opacity |
| --- | --- | --- | --- | --- | --- | --- | --- |
| 1 | MC1-SD-C1 | A1 | B1 | 79.2 | −4.0 | −3.2 | 45.9 |
| 2 | MC1-SD-C0 | A2 | B1 | 76.0 | −7.3 | −8.3 | 48.1 |

Upon mixing of the Pastes A1 and A2 with Paste B1, the b*-value of Example 1 and Example 2 decreased. A color shift from yellow to blue was observed. This proves that the pH-sensitive polymer of MC-SD-C1 (in Paste A1) reacted with the acidic paste, thereby releasing the blue dye Sudan II.

C Porous Microcapsules Filled With an Ascorbic Acid Component

The general principle of the production of microcapsules containing a reducing agent (e.g. ascorbic acid or derivative thereof) and coated with a shell of an acid-sensitive material is shown in FIGS. 2jA-C. The microcapsules were prepared as described above. The obtained microcapsules are shown in FIG. 2A.

Filling of Porous Microcapsules With Ascorbic Acid 5 g of ascorbic acid were dissolved in 30 g demineralized water. The filling was realized by dropping the solution containing ascorbic acid onto 30g of porous polymer particles MC1. The particles absorbed the solution containing ascorbic acid. The solvent was removed afterwards by drying at room temperature. These microcapsules are designated as MC1-AA-C0 and are shown in FIG. 2B.

Coating of Microcapsule

The filled porous microcapsules MC1-AA-C0 were coated with a coating agent via spray drying to form a shell on the microcapsule. The coating agent used was Eudragit™ EPO. The spray drying was performed at temperatures around the $T_g$ of the coating agent using a lab scale spray drier from Büchi, Type B 290 with an inlet temperature range of 55° C. to 60° C. Microcapsules as shown in FIG. 2C were obtained. The coated microcapsules are designated as MC1-AA-C2 respectively.

Extraction of Porous Microcapsules (Not Coated)

0.2 wt. % MC1-AA-C0 of the filled microcapsules were dispersed in 0.2M $H_3PO_4$ in water using a VORTEX™ mixer. Then, the mixture subjected to ultrasound treatment, centrifuged, and filtered to obtain a solution with extracted ascorbic acid derivatives. This sample solution was subsequently injected into an HPLC apparatus and the concentration of the ascorbic acid was determined.

Finding:

The determined amount of ascorbic acid was very close to the theoretical amount. This proves that the microcapsules described in the present text can reliably be filled with a reactive component.

What is claimed is:

1. A curable composition comprising:
   polymerizable components bearing a radically-polymerizable unsaturated group; and
   a microcapsule comprising:
      a hollow or porous core composed of a polymeric material,
      a component of a redox-initiator system, the component of a redox-initiator selected for use to initiate curing of the polymerizable components, and
      a shell composed of an acid-sensitive material, the acid-sensitive material characterized as being ionic as a result of pH values from 1-4,
      wherein the component of a redox-initiator system is encapsulated within the hollow or porous core, and
      p2 wherein the shell is at least partly coating the polymeric material.

2. The curable composition of claim 1, the polymeric material comprising a (meth) acrylate.

3. The curable composition of claim 1, the porous or hollow core being characterized by the following features alone or in combination:
   having a spherical shape;
   having a diameter in the range of 1 to 200 μm;
   having a pore size from 10 to 200 nm;
   being mechanically stable.

4. The curable composition of claim 1, the shell being characterized by the following features alone or in combination:
   thickness: 0.1 to 5 μm;
   covering more than 85% of the surface of the porous or hollow core;
   soluble in acidic or basic components.

5. The curable composition of claim 1, the acid-sensitive material being a polymer comprising co-polymer(s) of methyl (meth) acrylate and diethylaminoethyl (meth) acrylate, co-polymer(s) of methyl (meth) acrylate, butyl methacrylate and dimethylaminoethyl (meth) acrylate, or a combination thereof.

6. The curable composition of claim 1, wherein the component of a redox-initiator system is a reducing agent ascorbic acid comprising an ascorbic acid moiety.

7. The curable composition according to claim 1, wherein the component of a redox-initiator system is a reducing agent selected from ascorbic acid component(s), tertiary amine component(s), sulfinate component(s), sulphite component(s), borane component(s), (thio)urea component(s), and (thio)barbituric acid component(s), saccharin, and metal salts thereof.

8. The curable composition according to claim 1, wherein the component of a redox-initiator system is an oxidizing agent selected from hydroperoxide(s), ketone peroxide(s), diacyl peroxide(s), dialkyl peroxide(s), peroxyketal(s), peroxyester(s) and peroxydicarbonate(s), persulfate component(s) and mixtures thereof.

9. The curable composition of claim 1, being a dental composition or an orthodontic composition.

10. The curable composition of claim 1, being a dental or orthodontic cement, an adhesive, or a filling material.

11. A process of producing a curable composition of claim 1, the process comprising the steps of:
    providing a hollow or porous core;
    providing a component of a redox-initiator system;
    allowing the hollow or porous core to absorb the component of the redox-initiator system;
    coating the hollow or porous core containing the component of the redox-initiator system therein with an acid-sensitive material to form a microcapsule; and
    combining the microcapsule with polymerizable components.

12. The process of claim 11, the coating step being done by spray-drying at the glass transition temperature $T_g$ of the pH-sensitive material.

13. A kit of parts comprising a Catalyst Paste and a Base Paste,
    the Catalyst Paste comprising:
       a microcapsule comprising:
          a hollow or porous core composed of a polymeric material,
          a first component of a redox-initiator system, and
          a shell composed of an acid-sensitive material, the acid-sensitive material characterized as being ionic as a result of pH values from 1-4,
          wherein the first component of a redox-initiator system is encapsulated within the hollow or porous core, and
          wherein the shell is at least partly coating the polymeric material; and
    the Base Paste comprising:
       an acidic component or a basic component,
       a second component of a redox-initiator system.

14. The kit of parts according to claim 13, the Base Paste comprising an acidic component being characterized by the following features alone or in combination:
- pKs value: below 5;
- comprising an acidic moiety selected from a sulfonic, sulfinic, phosphoric, phosphonic, phosphinic, or carboxylic moiety;
- comprising one or more polymerizable moieties.

15. The kit of parts of claim 13,
- the Catalyst Paste further comprising:
  - curable non-acidic (meth) acrylate component(s),
  - filler(s),
  - optionally photo initiator(s),
- the Base Paste B further comprising:
  - curable (meth) acrylate component(s),
  - filler(s),
  - optionally transition metal component(s).

16. A process of curing a curable composition, the process comprising the steps:
- providing a kit of parts of claim 15,
- mixing the Catalyst Past and the Base Paste.

* * * * *